United States Patent [19]

Yiournas et al.

[11] Patent Number: 4,895,452

[45] Date of Patent: Jan. 23, 1990

[54] METHOD AND APPARATUS FOR PRODUCING LIPID VESICLES

[75] Inventors: Costas Yiournas, Vineland, N.J.; Donald F. H. Wallach, Brookline, Mass.

[73] Assignee: Micro-Pak, Inc., Wilmington, Del.

[21] Appl. No.: 163,806

[22] Filed: Mar. 3, 1988

[51] Int. Cl.$^4$ .............. B01F 3/08; B01F 5/06; B01F 15/02; B01J 13/02

[52] U.S. Cl. .................... 366/173; 366/165; 264/4.1

[58] Field of Search .............. 428/402.2; 264/4.1, 264/4.3; 366/165, 173; 425/5

[56] References Cited

U.S. PATENT DOCUMENTS

| | | | |
|---|---|---|---|
| 2,043,108 | 6/1936 | Maurer | 137/111 |
| 3,238,021 | 3/1966 | Webber et al. | 23/259.1 |
| 3,623,705 | 11/1971 | Townsley et al. | 366/165 |
| 3,844,721 | 10/1974 | Cariou et al. | 23/259.2 |
| 4,019,720 | 4/1977 | Levesque et al. | 259/4 R |
| 4,092,013 | 5/1978 | Staaf | 366/165 |
| 4,310,493 | 1/1982 | Pisaric et al. | 422/135 |
| 4,480,925 | 11/1984 | Dietrich | 366/107 |
| 4,533,254 | 8/1985 | Cook et al. | 366/176 |
| 4,621,023 | 11/1986 | Redziniak et al. | 428/402.2 |
| 4,684,574 | 8/1987 | Pietsch et al. | 428/402.2 |
| 4,753,788 | 6/1988 | Gamble | 264/4.1 X |
| 4,772,471 | 9/1988 | Vanlerberghe et al. | 428/402.2 X |
| 4,776,991 | 10/1988 | Farmer et al. | 264/4.1 X |

OTHER PUBLICATIONS

Dousset and Douste-Blazy, "Methodes de preparation des liposomes", in *Les Liposomes,* Puisieux and Delattre, Eds., Techniques et Documentation La Voisier Paris, pp. 41-70 (1980).

Szoka and Papahadjopoulos, "Procedure for Preparation of Liposomes with Large Internal Aqueous Space and High Capture by Reverse-Phase Evaporation", Proc. Natl. Acad. Sci U.S.A., 75:4194-4198 (1978).

*Primary Examiner*—John F. Terapane
*Assistant Examiner*—John M. Covert
*Attorney, Agent, or Firm*—Lahive & Cockfield

[57] ABSTRACT

The present invention provides an apparatus and method for manufacture of multilamellar or paucilamellar lipid vesicles. The apparatus and method use shear mixing in a substantially cylindrical mixing chamber having at least one tangential input for rapid production of the lipid vesicles.

4 Claims, 2 Drawing Sheets

METHOD AND APPARATUS FOR PRODUCING LIPID VESICLES

REFERENCE TO RELATED APPLICATION

This application is related to U.S. Pat. applications Ser. No. 025,525, filed Mar. 13, 1987, entitled "Method of Producing High Aqueous Volume Multilamellar Vesicles", U.S. Pat. application Ser. No. 078,658, filed July 28, 1987, entitled "Method of Producing High Aqueous Volume Multilamellar Vesicles", and U.S. Pat. application Ser. No. 124,824, filed Nov. 24, 1987, entitled "Lipid Vesicles Formed of Surfactants and Steroids", the disclosures of which are incorporated herein by reference.

BACKGROUND OF THE INVENTION

The present invention relates to a method and apparatus for producing lipid vesicles. More particularly, the invention is directed to a production technique that permits rapid, high volume formation of lipid vesicles from surfactants and other amphiphilic molecules.

Lipid vesicles are lipid structures which surround and encapsulate aqueous volumes. There are many uses for these structures, e.g., as adjuvants or as carriers for the transportation of encapsulated drugs or biologically-active substances. Lipid vesicles are often classified into three groups by size and structure: multilamellar vesicles ("MLV's"), large unilamellar vesicles ("LUV's"), and small unilamellar vesicles ("SUV's"). MLV's are onion-like structures having a series of substantially spherical shells formed of lipid bilayers interspersed with aqueous layers. LUV's have a diameter greater than 1 $\mu$ and are formed of a lipid bilayer surrounding a large, unstructured aqueous phase. SUV's are similar in structure to the LUV's except their diameters are less than 0.2 $\mu$.

A fourth type of lipid vesicle, which is particularly well suited for transport of either lipids or aqueous materials, is the paucilamellar vesicle ("PLV"). See, Callow and McGrath, *Cryobiology* 1985, 22(3), pp. 251–267. This type of vesicle has an external structure of about two to five peripheral lipid bilayers with a large, unstructured aqueous center. Lipid droplets, e.g., oil droplets, may be suspended in the aqueous center, leading to very high uptake of aqueous or lipophilic materials. Paucilamellar vesicles range from about 2–15 $\mu$ in diameter.

Each type of lipid vesicle has distinct advantages for certain uses. Because of the relatively large amount of lipid in the lipid bilayers of the MLV's, they are considered best for encapsulation or transportation of lipophilic materials. The LUV's, because of their large aqueous/lipid volume ratio, are considered best for encapsulation of hydrophilic molecules, particularly macromolecules. SUV's have the advantage of small size which allows relatively easy access to the cells of tissue, but their small volume limits delivery of hydrophilic aqueous materials to trace amounts. However, SUV's may be useful in place of MLV's for the transportation of small quantities of lipophilic materials because of high lipid/water ratios. PLV's can transport large quantities of aqueous or lipophilic materials but their large size can preclude approach to certain tissues.

The present invention pertains to the formation of MLV's and PLV's. Since SUV's are commonly made by sonication of multilamellar lipid vesicles, it follows that the processes by which MLV's are produced can be used as part of a technique for making SUV's.

The conventional approach to producing multilamellar lipid vesicles, particularly liposomes made of phospholipids, starts by dissolving the lipids, together with any lipophilic additives, in an organic solvent. The organic solvent is then removed by evaporation using heat or by passing a stream of an inert gas (e.g., nitrogen) over the dissolved lipids. The residue is then hydrated with an aqueous phase, generally containing electrolytes and additives such as hydrophilic biologically-active materials, to form large multilamellar lipid membrane structures. In some variations, different types of particulate matter or structures have been used during the evaporation process to assist in the formation of the lipid residue. Those in the field have shown that by changing the physical structure of the lipid residue, better vesicles form upon hydration. Two recent review publications, Szoka and Papahdjopoulos, Ann. Rev. Biophys. Bioeng. 9:467–508 (1980), and Dousset and Douste-Blazy (in *Les Liposomes*, Puisieux and Delattre, Editors, techniques et Documentation Lavoisier, Paris, pp.41–73 (1985)), summarize the methods which have been used to make MLV's.

No matter how the MLV's or PLV's are formed, once made it is necessary to determine the effectiveness of the process. Two measurements commonly used to determine the effectiveness of encapsulation of materials in lipid vesicles are the encapsulated mass and captured volume. The encapsulated mass is the mass of the substance encapsulated per unit mass of the lipid and is often given as a percentage. The captured volume is defined as the amount of the aqueous phase trapped inside the vesicle divided by the amount of lipid in the vesicle structure, normally given in ml liquid/g lipid.

A disadvantage associated with producing MUV's or PLV's using standard methods is that these processes are costly, slow and relatively inefficient in terms of material. For example, the standard time to manufacture MLV's is in the order 2–20 hours. If SUV's are required, the sonication which breaks the multilamellar lipid structures into SUV's takes additional time. This slow processing is unwieldy and expensive for any large scale production of lipid vesicles.

While rapid, continuous-flow, mixing processes are known in other arts, e.g., chemical kinetics, the adaptation of such processes for the production of lipid vesicles has not heretofore been devised, or even suggested.

Accordingly, an object of the invention is to provide an improved method and apparatus for making multilamellar or paucilamellar lipid vesicles.

A further object of the invention is to provide a lipid vesicle forming technique which lends itself to commercial, high-volume production.

Another object of the invention to provide a method and apparatus for the rapid, efficient encapsulation of biologically-active macromolecules into lipid vesicles.

These and other objects and features of the invention will be apparent from the following description and drawings.

SUMMARY OF THE INVENTION

The present invention features a method of producing multilamellar or paucilamellar lipid vesicles and an apparatus useful in their production. The method is based on the shear mixing of a solventless lipophilic phase, and a hydrophilic or aqueous phase in order to rapidly hydrate the lipophilic phase, thereby forming multilamellar or paucilamellar structures. The difference in structure is dependent, in part, on the choice of materials forming the lipophilic phase.

The method of the invention uses a mixing chamber having a substantially cylindrical inner surface with at least one substantially tangentially located inlet orifice which allow flow of one phase, preferably the lipid phase, into the hollow interior. An additional inlet orifice, which may be tangentially or substantially axially located, provides input of the other phase, preferably the aqueous phase. There is also a substantially axially located outlet orifice which allows removal of the lipid vesicles after formation.

The lipophilic phase is formed of a surfactant, preferably blended with a steroid such as cholesterol and an amphiphilic charge-producing material, as well as any lipophilic materials to be incorporated into the lipid vesicle. This lipophilic phase is injected into the mixing chamber through at least one of the inlet orifices. An aqueous phase, which contains primarily water or buffer and any hydrophilic materials to be incorporated into the lipid vesicle, enters the mixing chamber through a substantially tangentially located input orifice or an axially located inlet orifice. Both the lipophilic phase and aqueous phase are injected with sufficient force to create a rapid, substantially flow, preferably tangential, about the inner surface of the mixing chamber. The two streams of flowing liquid, the lipophilic phase and the aqueous phase, intersect in such a manner as to cause shear mixing, thereby forming the lipid vesicles. Turbulent flow for each liquid is preferred but may be unnecessary so long as the two phases intersect with sufficient force. The formed lipid vesicles are removed from the chamber through the axial outlet orifice and collected. In the preferred embodiment of the invention, two tangential flows of liquid intersect when traveling in the same direction, e.g., both clockwise or counter-clockwise about the inner surface of the mixing vessel. Depending on the pump speed, this flow allows shear mixing without causing excessive turbulence which would slow down the net flow. "Shear mixing" is defined as the mixing of the lipophilic phase with the aqueous phase under turbulent or shear conditions which provide adequate mixing to hydrate the lipid and form lipid vesicles. The pump speeds are modified depending on the viscosity of the materials and the size of the orifices selected. "Shear mixing" is achieved by liquid shear which is substantially equivalent to a flow rate for the combined phases of 5-30 m/s through a 1 mm radius orifice. In another embodiment of the invention, the two streams of fluid intersect by traveling in countercurrent directions, e.g., one clockwise and one counter-clockwise. This is most useful for very dilute solutions where excessive turbulence and resulting back pressure is not as much of a problem.

Preferred surfactants for use in the invention include polyoxyethylene acyl ethers, polyoxyethylene acyl amines, polyoxyethylene alkyl esters, polyoxyethylene sorbitan alkyl esters, and polyoxyethylene glycerol alkyl esters, where said alkyl or acyl groups have 16-20 carbon atoms and not more than two double bonds. Many of these materials are liquid at room temperature so no heating or other treatment step is necessary to achieve the fluid stage helpful for rapid flow. If the materials are not liquid at operating temperature, heating before introduction through the tangential inlet orifice is a preferred step since the liquid state provides proper flow about the mixing chamber.

Selection of the proper surfactant can modify the structure of the final lipid vesicles. Certain surfactants will form PLV's while others will form MLV's. Although not necessary to the invention, the difference is theorized to occur because of the differences in the lipophilic/hydrophilic balance of the surfactants.

The chamber should be made of materials which can withstand solutions which are heated above the melting point of the lipid. A chamber which will withstand 80° C. (a temperature high enough to melt substantially all of the lipids within this class) is helpful.

The invention also features a device for making lipid vesicles. The central part of this device is the mixing chamber with the inputs as previously described. In addition, this device should have reservoirs for the lipophilic and hydrophilic phases and pumps or drive mechanisms which force the phases, preferably in fluid form, through the inlet orifices into the mixing chamber. In addition, the inlet path from the reservoirs, or optionally the reservoirs themselves, can include mixing device insuring uniform dispersions of each of the lipophilic and aqueous phases. Another option is to have heaters, either within the reservoir or between the reservoir and the mixing chamber, to allow heating of the phases if necessary for proper liquid flow.

The specifics of the pumps, feed lines, and orifice size selection are a matter of engineering within the skill of those practicing the art and depend on amount and viscosity of the material to be processed and the desired flow rates.

These and other features of the invention will be more apparent from the drawings and the detailed description.

DETAILED DESCRIPTION OF PREFERRED EMBODIMENTS

As noted previously, the present invention features a method of making multilamellar or paucilamellar lipid vesicles and a device for the manufacture of those lipid vesicles. The methods and device have a mixing chamber with a substantially cylindrical interior surface as a central feature. This mixing chamber permits input of materials with controlled intersection of the lipophilic and hydrophilic phases in order to form the multilamellar or paucilamellar lipid vesicles. The term "substantially cylindrical" as used herein means and includes cylindrical, frustoconical and other shapes having substantially similar surfaces of revolution.

The following description will more clearly elucidate the principles of the invention.

1. The Mixing Chamber

Figure 1:
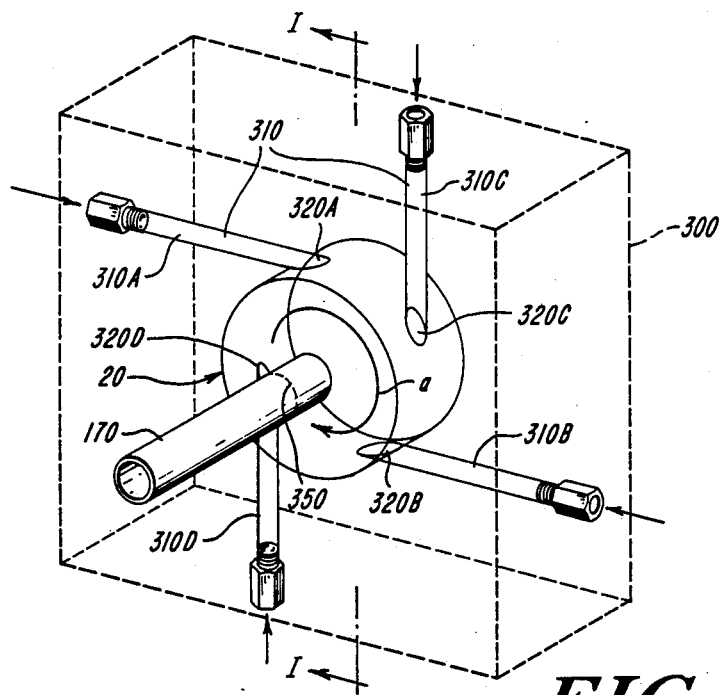
FIG. 1 is an perspective view of a mixing chamber for use in accordance with the practice of the invention.

A mixing chamber suitable in the present invention is shown in FIG. 1. Mixing chamber 20 has a substantially cylindrical cross-section forming a central, hollowed out portion of a block of material 300. Inlet feed lines, illustrated as 310A-310D, allow the lipophilic and aqueous phases to be injected into mixing chamber 20. Each of these inlet feed lines 310A–310D ends in an inlet orifice 320A–320D.

Figure 2:
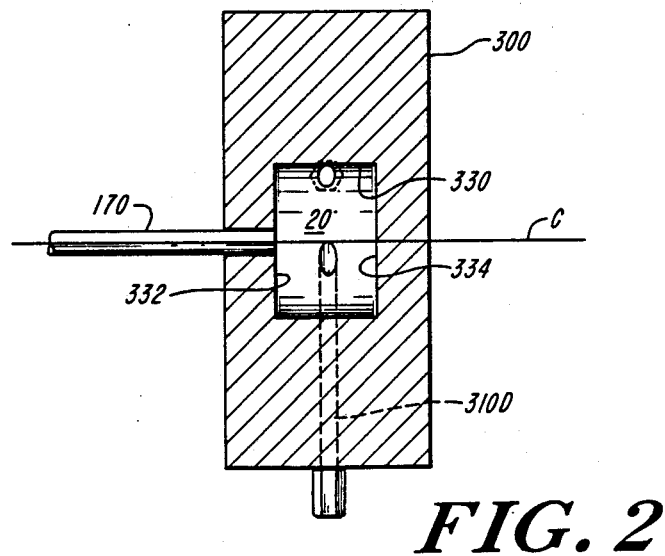
FIG. 2 is a sectional view taken along line I—I of the mixing chamber of FIG. 1.

FIG. 2 is a cross-sectional illustration of mixing chamber 20 about line I—I. As shown in FIGS. 1 and 2, mixing chamber 20 has a cylindrical inner surface 330 disposed about a central axis (designated "c") and is closed at each end by a circular face 332 and 334. Discharge orifice 350 is disposed through one of the circular faces, for example, as shown, through face 332. Discharge orifice 350, which preferably has of circular cross-section centered on the central axis c, has a diameter substantially less than that of the cylindrical surface 330. In this preferred embodiment, discharge orifice 350 is both axially and radially spaced from the inlet orifices 320A–320D.

Inlet orifices 320A–320D serve as injection jets and are arranged in spaced relation perpherally about mixing chamber 20. While it is preferred that inlet orifices 320A–320D, as well as inlet feed lines 310A–310D, are arranged in a plane disposed perpendicular to the central axis c of the cylindrical mixing chamber 20, this is not required. The four inlet orifices 320A–320D shown in FIG. 1 are spaced about the cylindrical inner surface 330 at ninety degree intervals and are tangential relative to cylindrical inner surface 330.

Lipid material is introduced into mixing chamber 20 through inlet orifices 320A and 320B which are connected to external feed lines 158 and 162 (FIG. 3) through inlet feed lines 310A–310B at diametrically opposite sides of cylindrical surface 330. The aqueous phase is introduced through inlet orifices 320C and 320D which are connected to external feed lines 160 and 164 (FIG. 3) through inlet feed lines 310C and 310D at diametrically opposite sides of cylindrical surface 330. With the illustrated arrangement, the fluids flow rotationally, as indicated by arrow "a", within the mixing chamber 20. All the fluids flow in the same direction, either clockwise or counter-clockwise, depending on whether viewed from face 332 or face 334.

The flow rates, volumes and particularly the flow paths are key to the efficient production of quality vesicles according to the invention. The fluids enter the mixing chamber 30 tangentially with respect to cylindrical wall 330, approximately 90° from the other inlet orifices. The fluid stream is guided in a spiral flow path from each injection orifice 310A–310D around the inner surface of the cylindrical wall 330, and then out through discharge orifice 350 into an exit tube 170. The flow paths are controlled by the orientation and placement of the injection orifices 310A–310D so as to intersect, creating the mixing zone. The pump speeds, as well as the orifice and feed line diameters, are selected to achieve proper shear mixing for lipid vesicle formation. In most circumstances, turbulent flow is selected to provide adequate mixing.

2. Pumo Driven Fluid Device

Figure 3:
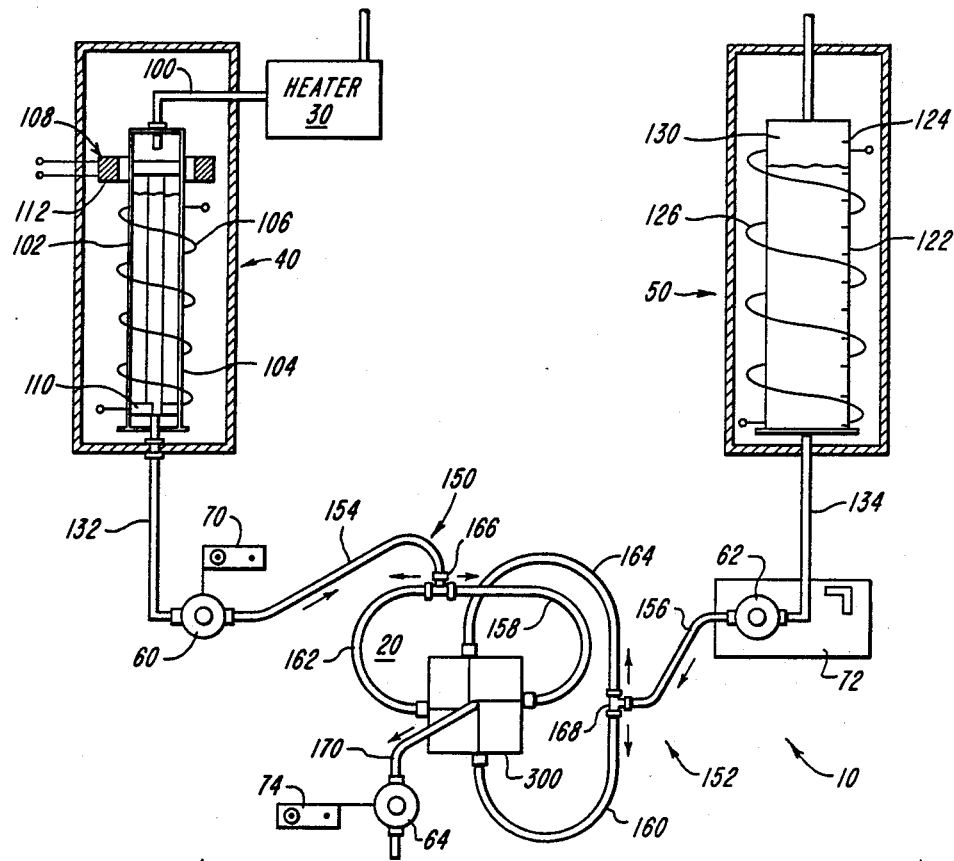
FIG. 3 is a schematic representation of a lipid vesicle producing apparatus in accordance with a first embodiment of the invention.

As noted previously, the mixing chamber is the heart of the apparatus for making the multilamellar or paucilamellar lipid vesicles. FIG. 3 illustrates one embodiment of the invention which uses this mixing chamber.

Mixing chamber 20 (not shown) is within block 300. The lipid reservoir 40 holds the lipophilic phase and the aqueous reservoir 50 holds the aqueous phase. Connected to the reservoirs and the outlet from the mixing chamber are the first, second and third pumps 60, 62 and 64 with their respective controllers 70, 72 and 74. Third pump 64 and its controller 74 are optional and are unnecessary under most circumstances.

The lipophilic phase, consisting the surfactant and the other lipophilic materials (e.g., a steroid such as cholesterol, a charge-producing amphiphile, and any lipophilic materials to be encapsulated) are blended and placed in lipid reservoir 40. Heater 30 is optional and is meant to illustrate any device which can preheat the lipophilic phase (if needed) to allow it to flow as a fluid at temperature of operation. Heater 30 may be a hot plate, an oven, or the entire apparatus may be placed in a warm room.

Preferably, the temperature of the lipid material within holding reservoir 40 is such that the lipid material remains in a fluid state. For lipid materials with melting points above room temperature, it maybe necessary to keep the material at elevated temperature within the reservoir. To that end, holding reservoir 40 can serve as an incubator, optionally having a warming element such as the illustrated heater coil 106 which is helically wound about the interior holding vessel 102, and/or a thermally insulating jacket enclosing holding vessel 102. In certain instances, it is desirable to melt the lipid material directly within holding reservoir 40 by employing warming element 106, thereby eliminating the need for separate heating device 30. If the lipid is a liquid at room temperature, no heating device is necessary.

Lipophilic additives, e.g., steroids such as cholesterol, are normally blended into the lipid before the lipophilic phase reaches holding reservoir 40. However, additives can be introduced directly into holding reservoir 40 and blended into the lipid. If so, a mixing device such as a magnetic or mechanical mixer 108 is provided. Illustrated mixer 108 has a vaned, mixing element 110 extending longitudinally within the vessel 102. Mixing element 110 is rotationally driven by a driver, such as a motor or an electromagnetic driving coil 112 disposed outside holding vessel 102, with which mixing element 110 is magnetically coupled.

Lipid reservoir 40 is coupled to the inlet of pump 60 by tubinq 132. Preferably, pump 60 is a positive displacement, magnetically driven pump. It is also preferred that the pump be detachable from its driving motors (not separately shown) for sterilizing, for example, by autoclaving. A suitable pump for the lipid material, for example, is made by Cole-Parmer, Model No. J-7002-23, coupled with motor drive Model No. 7144-04.

The output from pump 60 is connected to mixing chamber 20 by feed line 150. Feed line 150 is provided with a flow splitting or branch fitting arrangement 166 whereby first line 154 is connected to both external feed line 158 and external feed line 162. Feed line 150 has, for example, a ¼ inch (0.1 cm) outer diameter and a ⅛ inch (0.05 cm) inner diameter. All connections are preferably made with compression fittings, for example, of Teflon brand material which can be autoclaved at the same time as the lines.

Each of the external feed lines 158 and 162 are connected to inlet feed lines for the lipophilic phase, specifically inlet feed lines 310A and 310B, respectively.

FIG. 3 also illustrates the aqueous phase portion of the system. Aqueous reservoir 50 is similar in construction to lipid reservoir 40 except chamber 122 is larger because the aqueous volume added to hydrate the lipophilic phase is normally much larger than the lipid volume. Heater 126 is optional and is used normally if the aqueous phase is heated. This permits the reaction to take place without large temperature differences which provides better lipid vesicle formation.

The aqueous phase, including any additives or biologicals which are to be encapsulated, is placed in aqueous reservoir 50 and flows through tubing 134 to pump 62. Again, pump 62 is preferably a positive displacement, magnetically driven pump with a detachable drive motor. A Cole-Parmer Model No. J-7003-04 pump coupled with motor drive Model No. 7617-70 is a suitable pump for the aqueous phase.

The output of pump 62 is connected to feed line 150 which is then split at branch fitting 168 into external feed line 160 and external feed line 164. Lines 160 and 164 are attached to inlet feeds 310C and 310D, respectively, allowing the aqueous phase to enter mixing chamber 20.

In operation, pumps 60 and 62 drive the lipophilic phase and aqueous phase, respectively, into mixing chamber 20. In mixing chamber 20, shear mixing occurs, causing the formation of hydrated lipid which quickly coalesces into multilamellar or paucilamellar lipid vesicles. These lipid vesicles are withdrawn from mixing chamber 20 through exit tube 170. Removal of the vesicles may be enhanced, in certain instances, by the action of pump 64, preferably a vacuum pump.

Prototypical mixing chambers have been made in a block of Lucite brand plastic which fits into the palm of the hand. The cylindrical inner surface of the chamber has an 8 mm diameter with a 5 mm diameter discharge orifice 320. In this prototype, inlet orifices 310A-310D each have a 1 mm radius. In the tested system, two inlet orifices, 310A-310B are fed by the described pump 60 to deliver the lipid mixture to the chamber while the other two inlet orifices 310C-310D are fed by the other described pump 62 which delivers aqueous phase. The absolute and relative flow velocities are controlled to give lipid vesicles of desired properties. Water-soluble materials to be encapsulated are included in the aqueous phase, and lipophilic materials in the lipid phase. Lipid vesicles can be fashioned in less than a second when the preferred linear flow rate of at least 10 m/s is used. Actual flow of the materials can be adjusted to optimize the process. For example, for an aqueous flow rate of 1.9 l/minute, the lipid mixture flow rate is selected between a rate of 472 ml/mm for low hydration and a rate of 94 ml/minute for high hydration.

3. Syringe Driven System

Figure 4:
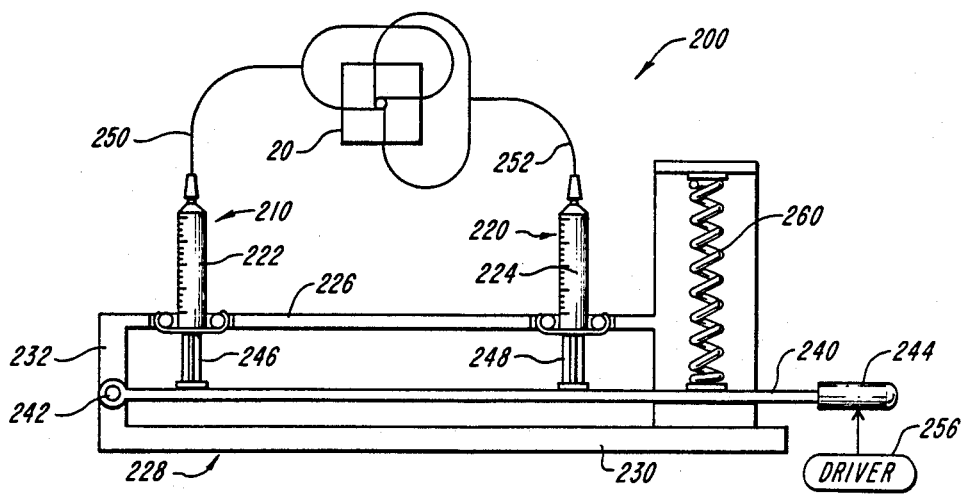
FIG. 4 is a schematic representation of a lipid vesicle producing apparatus in accordance with a second embodiment of the invention.

FIG. 4 shows an alternative embodiment for forming lipid vesicles. Instead of motor-driven pumps to drive the fluid, apparatus 200 has a lever arrangement for operating syringes 210 and 220. Raising the lever injects the lipid material and the aqueous phase into mixing chamber 20 where it meets and forms lipid vesicles.

More specifically, syringes 210 and 220, preferably of conventional construction, have barrels 222 and 224 for holding the lipid and aqueous phases, respectively. As shown, barrels 222 and 224 are mounted on a support member 226 of a platform 228.

For example, the barrels 222 and 224 can be held by clamps 229 which are also releasably clampable to the support member 226. Other arrangements incorporating different setting mechanisms, e.g., ratcheting, detent and retention elements, will be apparent to one skilled in the art. A horizontal base 230 supports the platform 228, and, as illustrated, extends in spaced, generally parallel relation to the support member 226. A vertical linking member 232 interconnects the syringe support member 226 and the base 230, as shown, at a first end of each.

Syringes 210 and 220 are operated by manually raising lever arm 240. As shown, lever arm 240 is pivotally connected at one end to linking member 232 by pivot connection 242 which serves as a fulcrum and, at the other end, extends longitudinally beyond the support member 226, culminating in a handle 244. Illustrated lever arm 240 is disposed in the space between the support member 226 and the base 230 for vertical angular motion. As lever arm 240 is pivoted upwards from its horizontal position, it drives syringe plungers 246 and 248 into the respective syringe barrels 222 and 224, injecting the fluid materials contained therein into feed tubing 250 and 252 for delivery to mixing chamber 20.

As illustrated, near the handle 242 is a biasing spring 260 which provides restoring force to drive lever arm 240 downwardly to its preferably horizontal, ready position, and maintains lever arm 240 in the horizontal position when not actuated. Lever arm 240 can be actuated manually, or by an optional driver 256, such as a linear motor.

This apparatus provides proportional injection of the fluids from syringes 210 and 220. As will be apparent to one skilled in the art, the extent of displacement of the plungers 246 and 248 into barrels 222 and 228 is proportional to the vertical displacement of lever arm 240 at plungers 246 and 248. This, in turn, is proportional to the distance from pivot connection 242 to respective plungers 246 and 248. Thus, if all else is equal, by placing the lipid material in syringe 210 and buffer in syringe 220, more buffer than lipid material is injected since syringe 210 is closer than syringe 220 to pivot connection 242. By proper placement of the syringes 210 and 220 along the support member 226, a selected ratio of buffer to lipid material can be controllably injected.

Both of the described drive mechanisms can be used with the same mixing chamber and perform the method of the invention. Other types of drive apparatus and modifications in the mixing chamber can be used in the methods of the invention. Such other modifications, including modifications of the apparatus, will be readily apparent to one skilled in the art. Such other modifications are included within the following claims.

What is claimed is:

1. An apparatus for the production of multilamellar or paucilamellar lipid vesicles by shear mixing and rapid hydration of a lipophilic phase by a hydrophilic phase, said apparatus comprising:

a substantially hollow mixing chamber having an interior surface, an exterior surface, and a cross-section which is substantially cylindrical about a first axis, said mixing chamber further containing a first inlet orifice for inlet of said lipophilic phase, a second inlet orifice for inlet of said hydrophilic phase, and an outlet orifice, said first inlet orifice and said second inlet orifice being located substantially tangential to said inner surface of said mixing chamber and said first and second inlet orifices being directed in the same tangential direction, said outlet orifice being located substantially axial along said first axis, said outlet being free of any turbulence-creating barriers;

a first reservoir for holding said lipophilic phase;

a free delivery system for delivering said lipophilic phase from said first reservoir to said first inlet orifice, said first delivery system comprising a first pump, a first inlet feed line connecting said first pump to said first inlet orifice, and a first tubing connecting said first reservoir to said first pump;

a second reservoir for holding said hydrophilic phase; and a second delivery system for delivering said hydrophilic phase from said second reservoir to said second said inlet orifice, said second delivery system comprising a second pump, a second inlet feed line connecting said second pump to said second inlet orifice, and a second tubing connecting said second reservoir to said second pump;

said first and second pumps, said first and second tubing, said first and second inlet feed lines, and said first and second inlet orifices being selected in size to provide shear mixing by introducing said lipophilic phase and said hydrophilic phase into said hollowing mixing chamber with sufficient velocities such that turbulent flow is created in said hollow mixing chamber, thereby providing shear mixing and hydration of said lipophilic phase by said hydrophilic phase in said hollow mixing chamber.

2. The apparatus of claim 1 wherein said first reservoir comprises a first holding tank and a first heater.

3. The apparatus of claim 1 wherein said second reservoir comprises a second holding tank and a second heater.

4. The apparatus of claim 1 wherein said mixing chamber comprises a plurality of said first inlet orifices and a plurality of said second inlet orifices.

* * * * *